(12) United States Patent
Kimura

(10) Patent No.: US 9,924,887 B2
(45) Date of Patent: Mar. 27, 2018

(54) MEDICAL IMAGE DISPLAY APPARATUS

(75) Inventor: Tokunori Kimura, Yaita (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 2036 days.

(21) Appl. No.: 11/212,571

(22) Filed: Aug. 29, 2005

(65) Prior Publication Data

US 2006/0058624 A1    Mar. 16, 2006

(30) Foreign Application Priority Data

Aug. 30, 2004    (JP) .................................. 2004-250182

(51) Int. Cl.
*A61B 5/055*    (2006.01)
*A61B 5/00*    (2006.01)

(52) U.S. Cl.
CPC ............ *A61B 5/055* (2013.01); *A61B 5/7425* (2013.01); *A61B 5/7445* (2013.01); *A61B 5/743* (2013.01)

(58) Field of Classification Search
CPC .... G06F 3/0482; G06F 3/0483; G06F 19/321; A61B 5/055; A61B 5/7425; A61B 8/465
See application file for complete search history.

(56) References Cited

U.S. PATENT DOCUMENTS

| | | | | |
|---|---|---|---|---|
| 5,410,250 A | * | 4/1995 | Brown ........................... | 324/309 |
| 5,433,199 A | * | 7/1995 | Cline ................. | G01R 33/5608 600/413 |
| 5,954,650 A | * | 9/1999 | Saito ....................... | G06T 11/00 382/128 |
| 5,982,953 A | * | 11/1999 | Yanagita et al. .............. | 382/294 |
| 5,987,094 A | * | 11/1999 | Clarke ................. | G01N 23/046 378/62 |
| 5,987,345 A | * | 11/1999 | Engelmann ........... | G06F 19/321 128/920 |
| 6,016,439 A | * | 1/2000 | Acker ........................... | 600/411 |
| 6,081,267 A | * | 6/2000 | Stockham et al. ............. | 715/788 |
| 6,120,465 A | * | 9/2000 | Guthrie .................. | A61B 19/52 600/587 |
| 6,407,757 B1 | * | 6/2002 | Ho ................................ | 715/776 |

(Continued)

FOREIGN PATENT DOCUMENTS

| | | |
|---|---|---|
| JP | 59-17332 | 1/1984 |
| JP | 62-253043 | 11/1987 |

(Continued)

OTHER PUBLICATIONS

GE Medical System, Technical Publication, Discovery LS PET CT Combined PET and CT Scanner Operator's Guide, Direction 2288677-100, Rev. 5, Oct. 2003.*

(Continued)

*Primary Examiner* — Bo J Peng
(74) *Attorney, Agent, or Firm* — Nixon & Vanderhye P.C.

(57) ABSTRACT

There is provided a medical image display apparatus comprising a storage unit which stores data of a plurality of different types of medical images including the same region of a subject to be examined which are generated by the same type of image generating device, and a display control unit which displays the plurality of medical images at substantially the same position on a screen while sequentially switching the medical images one by one.

24 Claims, 5 Drawing Sheets

(56) References Cited

U.S. PATENT DOCUMENTS

| | | | | |
|---|---|---|---|---|
| 6,498,486 | B1* | 12/2002 | Ookawa | 324/312 |
| 6,633,689 | B2* | 10/2003 | Yamamoto | 382/309 |
| 6,674,449 | B1* | 1/2004 | Banks | A61B 5/055 345/625 |
| 7,570,985 | B2* | 8/2009 | Takabayashi et al. | 600/420 |
| 2001/0009369 | A1* | 7/2001 | Shimo et al. | 324/307 |
| 2002/0023067 | A1* | 2/2002 | Garland | G06F 17/3028 |
| 2002/0057386 | A1* | 5/2002 | Otera | G09G 5/00 348/744 |
| 2002/0090119 | A1* | 7/2002 | Saito et al. | 382/128 |
| 2003/0092981 | A1* | 5/2003 | Deimling | A61B 5/055 600/410 |
| 2003/0095147 | A1* | 5/2003 | Daw | G01R 33/56 715/771 |
| 2004/0061889 | A1* | 4/2004 | Wood et al. | 358/1.15 |
| 2004/0254445 | A1* | 12/2004 | Bittner | 600/410 |
| 2005/0238218 | A1* | 10/2005 | Nakamura | 382/128 |
| 2005/0285812 | A1* | 12/2005 | Shimayama et al. | 345/1.1 |

FOREIGN PATENT DOCUMENTS

| | | |
|---|---|---|
| JP | 5-81353 | 4/1993 |
| JP | 7-204170 | 8/1995 |
| JP | 7-239935 | 9/1995 |
| JP | 8-76741 | 3/1996 |
| JP | 8-336517 | 12/1996 |
| JP | 9-35043 | 2/1997 |
| JP | 9-98961 | 4/1997 |
| JP | 10-137190 | 5/1998 |
| JP | 10-305015 | 11/1998 |
| JP | 2001-155019 | 6/2001 |
| JP | 2002-34948 | 2/2002 |
| JP | 2002-301065 | 10/2002 |
| JP | 2003-135452 | 5/2003 |
| JP | 2003-529406 | 10/2003 |
| JP | 2004-41694 | 2/2004 |
| JP | 2004-173910 | 6/2004 |
| JP | 2004-201789 | 7/2004 |
| JP | 2004-215961 | 8/2004 |

OTHER PUBLICATIONS

Toga et al., The role of image registration in brain mapping. Image Vis Comput. Jan. 1, 2001; 19(1-2): 3-24.*

John VanMeter, Lab-02, Gradient echo T1 & T2 Curves, Jul. 2004.*

Ratib, Abstract of *PET/CT Image Navigation and Communication*, The Journal of Nuclear Medicine, 2004, vol. 45, No. 1 (Suppl) 46S-55S, Abstract only.

Friston et al., *Spatial registration and normalization of images*, Human Brain Mapping 2, 1995, pp. 165-189.

Office Action dated Mar. 8, 2011 in Japanese Application No. JP 2005-231019 with English translation.

Office Action dated Jun. 11, 2013 in JP 2011-101748 with English translation.

Office Action dated Oct. 30, 2012 in JP 2011-101748 with English translation.

\* cited by examiner

Multi-frame display mode

Combination of single frame display direction and sequence

MEDICAL IMAGE DISPLAY APPARATUS

CROSS-REFERENCE TO RELATED APPLICATIONS

This application is based upon and claims the benefit of priority from prior Japanese Patent Application No. 2004-250182, filed Aug. 30, 2004, the entire contents of which are incorporated herein by reference.

BACKGROUND OF THE INVENTION

1. Field of the Invention

The present invention relates to a medical image display apparatus.

2. Description of the Related Art

A magnetic resonance imaging device (MRI device) as a medical image generating device can take a large variety of images such as longitudinal relaxation enhancement (T1) images, transverse relaxation enhancement (T2) images, proton density images, fluid attenuated inversion recovery (FLAIR) images, fat suppression images, diffusion weighted imaging (DWI) images, perfusion weighted imaging (PWI) images, functional images (f-MRI images), and magnetic resonance (MR) spectroscopy (MRS) images. An X-ray computed tomographic (CT) imaging device (X-ray CT) is sometimes used to take a plurality of types of functional images such as blood flow images as well as general anatomical images based on CT values. In many cases, films are arranged side by side and displayed on a viewing screen. An increasing number of apparatuses are designed to capture multi-modality images of the same subject to be examined and display them.

In performing radiographic interpretation, a doctor displays a plurality of types of images concerning the same region upon arranging them on a film or monitor, and observes them while moving his/her viewpoint to a place corresponding to the same anatomical region. Methods of comparing monochrome or color images upon superimposing them (fusion method) instead of arranging them at different positions have already been reported and generally used in X-ray CT, SPECT (Single Photon Emission Computed Tomography), and PET (Positron Emission Computed Tomography) (see non-patent references 1 and 2). Such methods have already been executed in MRI by using products on the market and free software for f-MRI and MRS (see non-patent reference 3).

In a current radiographic interpretation technique based on "diagnosis by arranging and comparing a plurality of types of images", since a doctor interprets a plurality of types of images while moving his/her viewpoint, eye strain occurs, resulting in requiring a long period of time for radiographic interpretation. This situation also applies to the monitor of a display apparatus instead of films. In addition, when images are compared with each other upon being arranged side by side, since the viewpoint of the doctor moves, it is difficult to perform diagnosis by anatomically precise comparison. In some dynamic display technique, images are sequentially displayed in the same frame in a spatial slice direction or time axis direction due to the situation in which the corresponding logical files are arranged on a disk or display memory in the corresponding direction. However, such a function is not created as an intentional function, and hence images cannot be displayed in various orders. Although a multi-frame display technique is available, frames are arranged in a slice direction or parameter direction.

In many cases, images to be compared are arranged at anatomically different slice positions because of limitations on imaging conditions. In addition, in echo planar imaging (EPI) and the like, the distortions of images are large as compared with spin echo (SE) images and the like, and hence it is difficult to compare the images.

When sensed images are to be simply displayed side by side, images vary in luminance or color unless they are normalized depending on the target. This makes it difficult to objectively observe the images. In the case of an MR technique, it is said that luminance information can be determined at about three levels at best, namely white, gray, and black. According to the fusion method, since images are superimposed on each other, one of images to be superimposed is limited to one which has a small spatial resolution or locality. In some cases, when, for example, images each having constant as a whole, e.g., T1 enhancement images and T2 enhancement images which are routinely used in MRI, are to be superimposed, it is difficult to grasp their relationship. The number of types of images which can be discriminated after they are superimposed on each other is two at best. This technique is not suitable for the types of images which are not generally colored. The following are the main prior art references:

Ratib O, "PET/CT image navigation and communication", Jnucl Med. Jan; 45 Suppll: 46S-55S (2004), Joseph Hajnal, D. J. Hawkes, Derek Hill, J V Hajnal, "Medical Image Registration", CRC Press, and Friston K J, Ashburner J, Poline J B, Frith C D, Heather J D, Frackowiak R S J, "Spatial Registration and Normalization of Images Human Brain Mapping 2," 165-189 (1995).

BRIEF SUMMARY

It is an object of the present invention to improve image diagnosis efficiency in a medical image display apparatus.

According to a first aspect of the present invention, there is provided a medical image display apparatus comprising a storage unit which stores data of a plurality of different types of medical images concerning the same region of a subject to be examined which are generated by the same type of image generating device, and a display unit which displays the plurality of medical images at substantially the same position on a screen while sequentially switching the medical images one by one.

According to a second aspect of the present invention, there is provided a medical image display apparatus comprising a storage unit which stores data of a plurality of medical images concerning the same region of a subject to be examined which are generated by an image generating device in different periods, and a display unit which displays the plurality of medical images at substantially the same position on a screen while sequentially switching the medical images one by one.

According to a third aspect of the present invention, there is provided a medical image display apparatus comprising a storage unit which stores data of a plurality of medical images concerning the same region, which includes at least one medical image concerning a subject to be examined which is generated by an image generating device and at least one medical image concerning a target other than the subject, and a display unit which displays the plurality of medical images at substantially the same position on a screen while sequentially switching the medical images one by one.

According to a fourth aspect of the present invention, there is provided a medical image display apparatus comprising a storage unit which stores data of a plurality of medical images, with different imaging parameter values concerning the same region of a subject to be examined and generated by the same type of image generating device, and a display unit which displays the plurality of medical images at substantially the same position on a screen while sequentially switching the medical images one by one.

According to a fifth aspect of the present invention, there is provided a medical image display apparatus comprising a storage unit which stores data of a plurality of medical images concerning the same region of a subject to be examined, a display unit which displays the plurality of medical images at substantially the same position on a screen while sequentially switching the medical images one by one, and an operation unit which changes a switching rule for switching the plurality of medical images to another switching rule.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below with reference to the views of the accompanying drawing.

Figure 1:
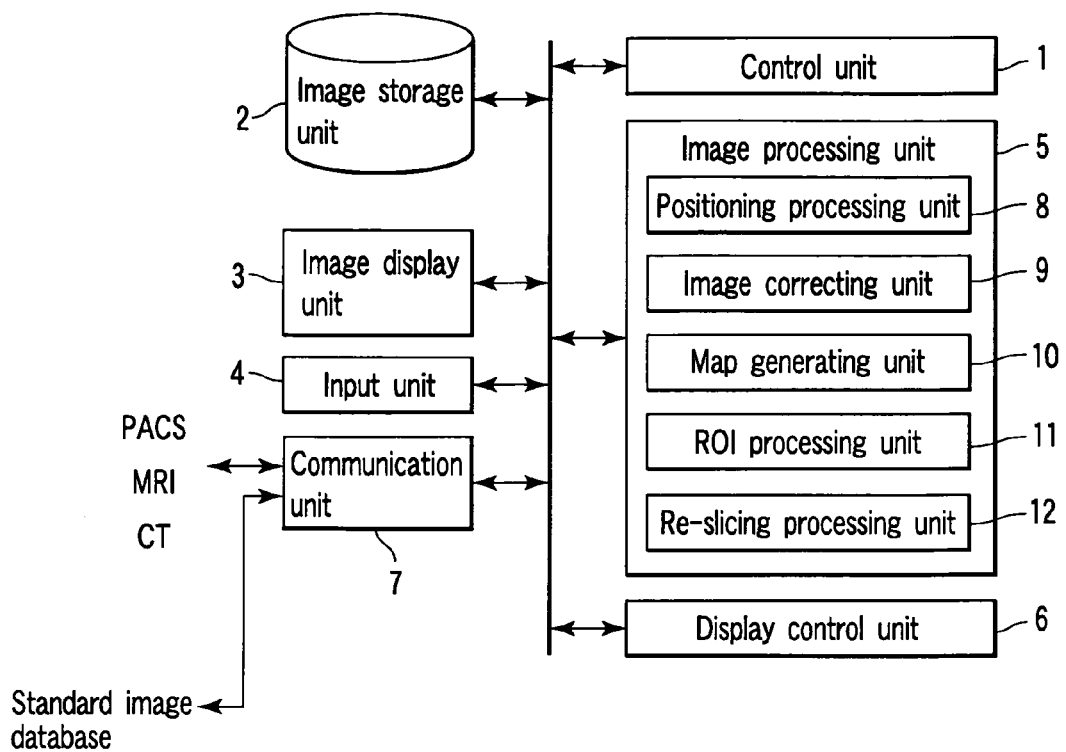
FIG. 1 is a block diagram showing the arrangement of an image display apparatus according to an embodiment of the present invention.

A medical image display apparatus according to this embodiment shown in FIG. 1 is an apparatus called a viewer which is associated with display of medical images generated by a medical image generating device such as an MRI device (magnetic resonance imaging device), X-ray CT device (X-ray computed tomography device), ultrasound diagnostic device, SPECT device (single photon emission computed tomography device), PET device (positron emission tomography device), or endoscope. The medical image display apparatus according to this embodiment is connected to an image database such as a picture archiving communication system (PACS) and image generating devices such as an MRI device and X-ray CT device through a communication unit 7, and receives data of a plurality of medical images to be interpreted from the image database and the image generating devices. Medical image data are typically tomographic or projection images, and also include multi-slice tomographic images and volume data expressed in voxel. A plurality of medical images are stored in an image storage unit 2. A plurality of medical images differ in at least one of subject, imaging parameter, slice position (imaging position), and imaging period (or imaging time). In the case of MRI (magnetic resonance imaging), imaging parameters include the type of imaging sequence (pulse sequence), an echo time TE in the imaging sequence, a repetition time TR, the width and amplitude of an RF pulse, the width and amplitude of a gradient field pulse, and the like.

The plurality of medical image data stored in the image storage unit 2 include a plurality of medical image data of different types concerning the same region of a subject to be examined which are generated by image generating devices of the same type. In addition, the plurality of medical image data stored in the image storage unit 2 include current medical image data and past medical image data concerning the same region of a subject to be examined, e.g., data generated two weeks ago, which are generated in different periods by the same image generating device or image generating devices of the same type. In addition, the plurality of medical image data stored in the image storage unit 2 include reference images (standard images) concerning other subjects and standard phantoms and the like.

For the sake of descriptive convenience, a longitudinal relaxation enhancement image, transverse relaxation enhancement image, and proton density image concerning the same region of the same subject to be examined which are generated by an MRI device will be exemplified as display target images.

In addition to the communication unit 7 and image storage unit 2, the medical image display apparatus according to this embodiment includes a control unit 1 serving as a central unit for the overall apparatus, an image display unit 3, an input unit 4, and an image processing unit 5 which performs processing to be described later with respect to a display target image, and a display control unit 6 which controls the image display unit 3 to display the image processed by the image processing unit 5 on the image display unit 3 in the manner described later.

The image processing unit 5 includes a positioning processing unit 8 which anatomically positions a plurality of display target images and substantially unifies the sizes of images and the directions of slices as needed, an image correcting unit 9 which reduces variations in gain and variations in pixel value due to imaging parameters, a map generating unit 10 which generates a map using, as pixel values, the ratios or differences between a display target image and a reference image concerning the same region, a region of interest (ROI) processing unit 11 which generates a graphical pattern or the like representing changes between medical images concerning the ratios or differences between pixel values in a region of interest (ROI) or between the pixel values and standard pixel values in the corresponding region, and a re-slicing processing unit 12 which reconstructs a tomographic image as a display target image from a multi-slice tomographic image or volume data. Note that the above reference image is typically an image obtained by imaging the same subject in the past or a standard image concerning a normal or abnormal case which has been statistically processed. A standard image is generated for each disease.

The main functions of the medical image display apparatus and a display sequence according to this embodiment will be described below.

(1) Image Display Function (Display Control Unit 6)

Figure 2:
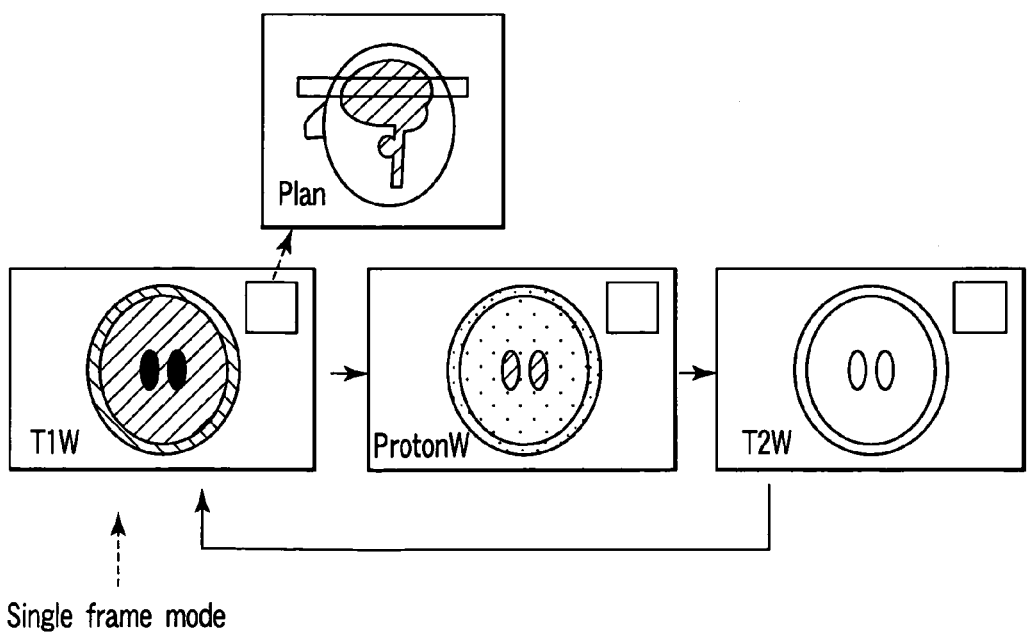
FIG. 2 is a view showing an image switching rule executed by a display control unit in FIG. 1.

As shown in FIG. 2, the display control unit 6 sequentially displays a plurality of display target images stored in the image storage unit 2, e.g., three types of MRI images concerning the same region of the same subject and same slice, like turning pages, at predetermined time intervals while the display position of each image on the screen of the image display unit 3 is almost fixed. Switching and displaying the display target images at the same position (making the center of each image coincide with a specific position on the screen) on the screen of the image display unit 3 while matching the anatomical positions of the respective images to each other. While interpreting the images with attention being focused on a special portion of the subject, the doctor can grasp with which kinds of shading the corresponding portion is displayed on a plurality of types of display target images while fixing his/her viewpoint at a specific position on the screen.

Display conditions such as an image display area on the screen and time intervals for image switching are preset and are manually adjusted through the input unit 4 as needed. If necessary, depending on conditions for images to be displayed, anatomical positioning between the display target images is performed two- or three-dimensionally by the positioning processing unit 8, and the sizes and forms of the images are corrected.

Figure 3A:
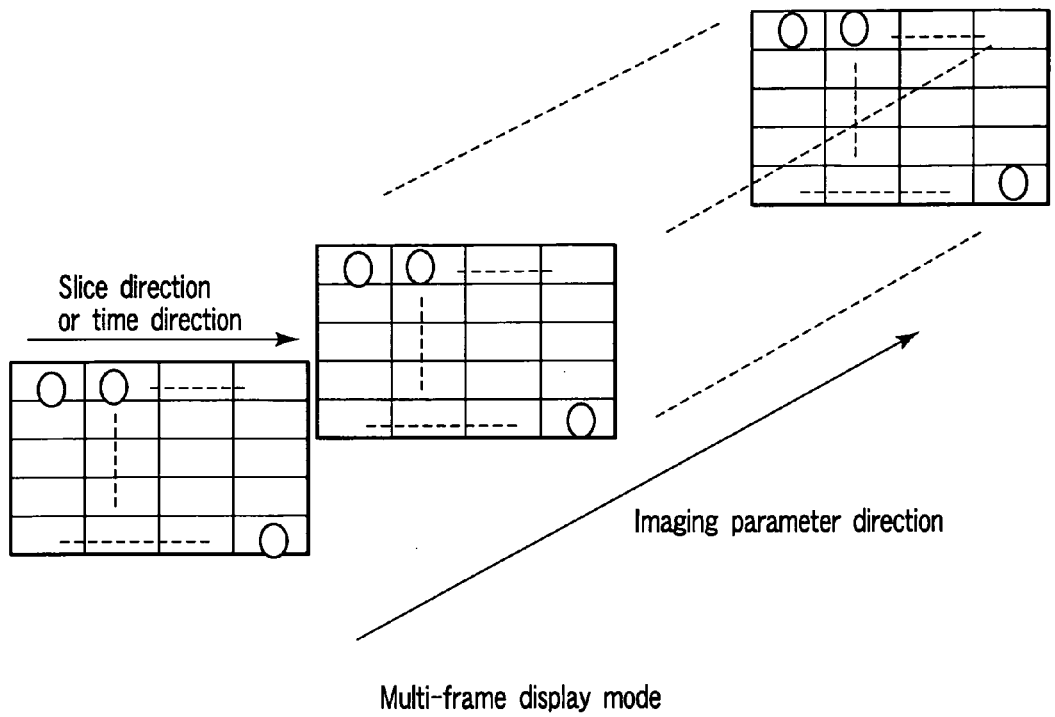
FIGS. 3A and 3B are views showing another image switching rule executed by the display control unit in FIG. 1.
Figure 3B:
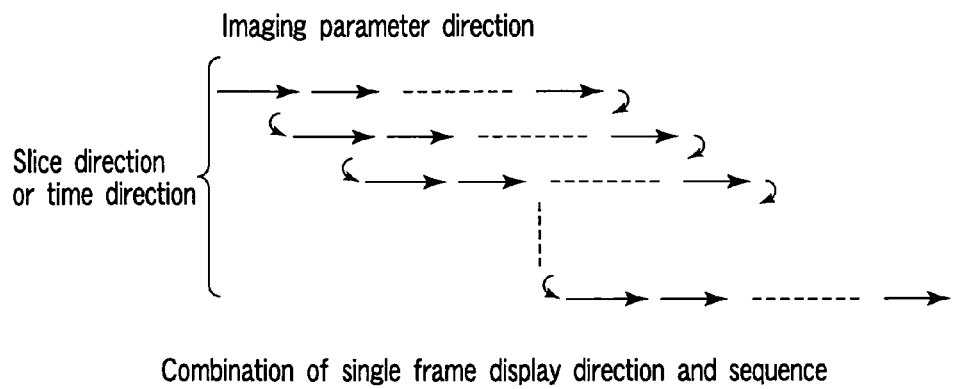

As shown in FIG. 2, images may be switched within a single window area (single frame) in accordance with imaging parameters. As shown in FIG. 3A, a window may be divided into a plurality of window elements (multi-frame). A plurality of images taken at different slice positions or different imaging times may be arranged and displayed in the plurality of window elements, and may be switched within each window area in accordance with imaging parameters. Alternatively, as shown in FIG. 3B, images may be switched within a single frame in accordance with imaging parameters. Thereafter, the slice position or imaging time may be shifted to switch images at the slice position or imaging time in accordance with imaging parameters. This operation may be repeatedly performed.

The display functions of the display control unit 6 include the following modes:

a) The functions concerning display transition include a mode of switching the currently displayed display target image to the next display target image with a fade-in/fade-out effect and a mode of instantaneously switching the currently displayed display target image to the next display target image. The fade-in/fade-out mode makes it easier than the mode of instantaneously switching images to compare the images before and after switching.

b) There are provided a manual mode of manually triggering the timing of display transition and an auto animation mode of repeating automatic, sequential switching of display target images at a rate of 1 to 30 frames per second like animation. When the auto animation mode is selected, periodic repetition of switching allows to repeat a comparative check. The rate can be manually adjusted.

The instantaneous switching mode or fade-in/fade-out switching mode can be selected.

c) Mapping Processing (Map Generating Unit 10)

This is a function of generating a map from the ratios or differences between a display target image and a reference image concerning the same region. The resultant image can be displayed in place of the original display target image (to be also referred to as an absolute value image). Reference images are stored in the image storage unit 2 in advance or may be acquired from an external standard image database through an Internet line. Reference images include a past image concerning the same subject, a standard image concerning the same disease in the same region, and a normal standard image concerning the same region. The database allows not only comparison with values based on normal people but also comparison with a database generated for each specific disease. In the future, this technique can be developed into computer aided diagnosis (CAD) techniques.

d) Region-of-Interest Processing (ROI Processing Unit 11)

Figure 5A:
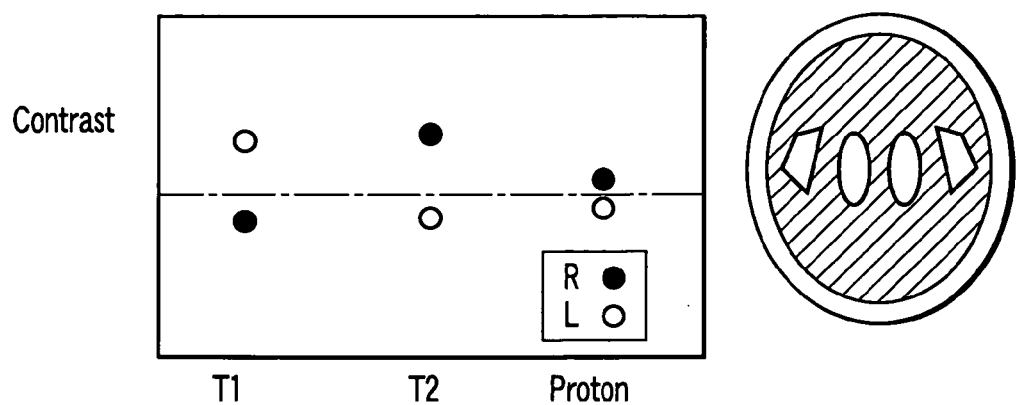
FIGS. 5A and 5B are views each showing an example of display of a processing result obtained by a region of interest (ROI) processing unit in FIG. 1.
Figure 5B:
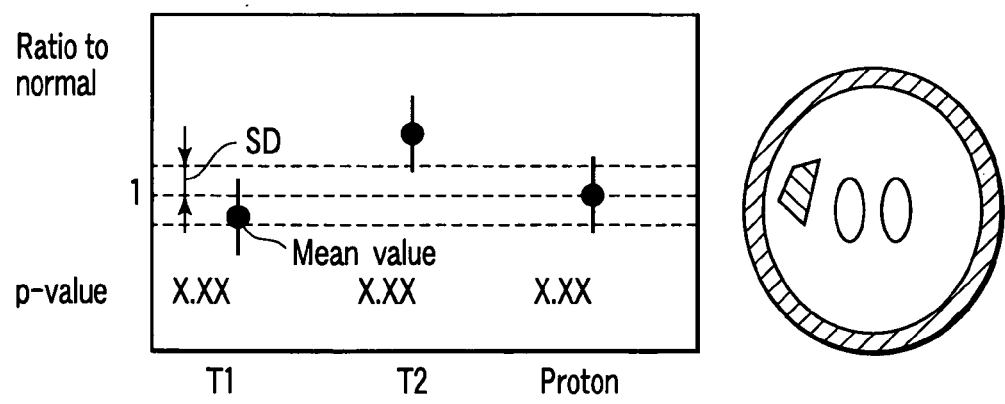

The input unit 4 is properly operated to generate a graphic pattern representing changes in pixel value or derived value in a region of interest (ROI) set on a display target image or map (see FIGS. 5A and 5B). This graphic pattern can be displayed in place of the original display target image (absolute value image) or map. The derived value is typically the mean value of the pixel values of a plurality of pixels in an ROI, a standard deviation (SD), and a skewness. When a display target image is selected in accordance with an imaging parameter difference, the relationship between the imaging parameter and the pixel value is expressed. When a display target image is selected in accordance with an imaging time difference, a temporal change in pixel value (a process of lesion) is expressed. In addition, when an organ is divided into areas and ROIs are set in the respective divided areas, changes in pixel value or derived value between the divided areas are generated. For example, an organ is divided into a liver zone, lung zone, cerebral blood vessel dominant area, an innervation function, and the like.

An image display sequence will be described next.

Figure 4:
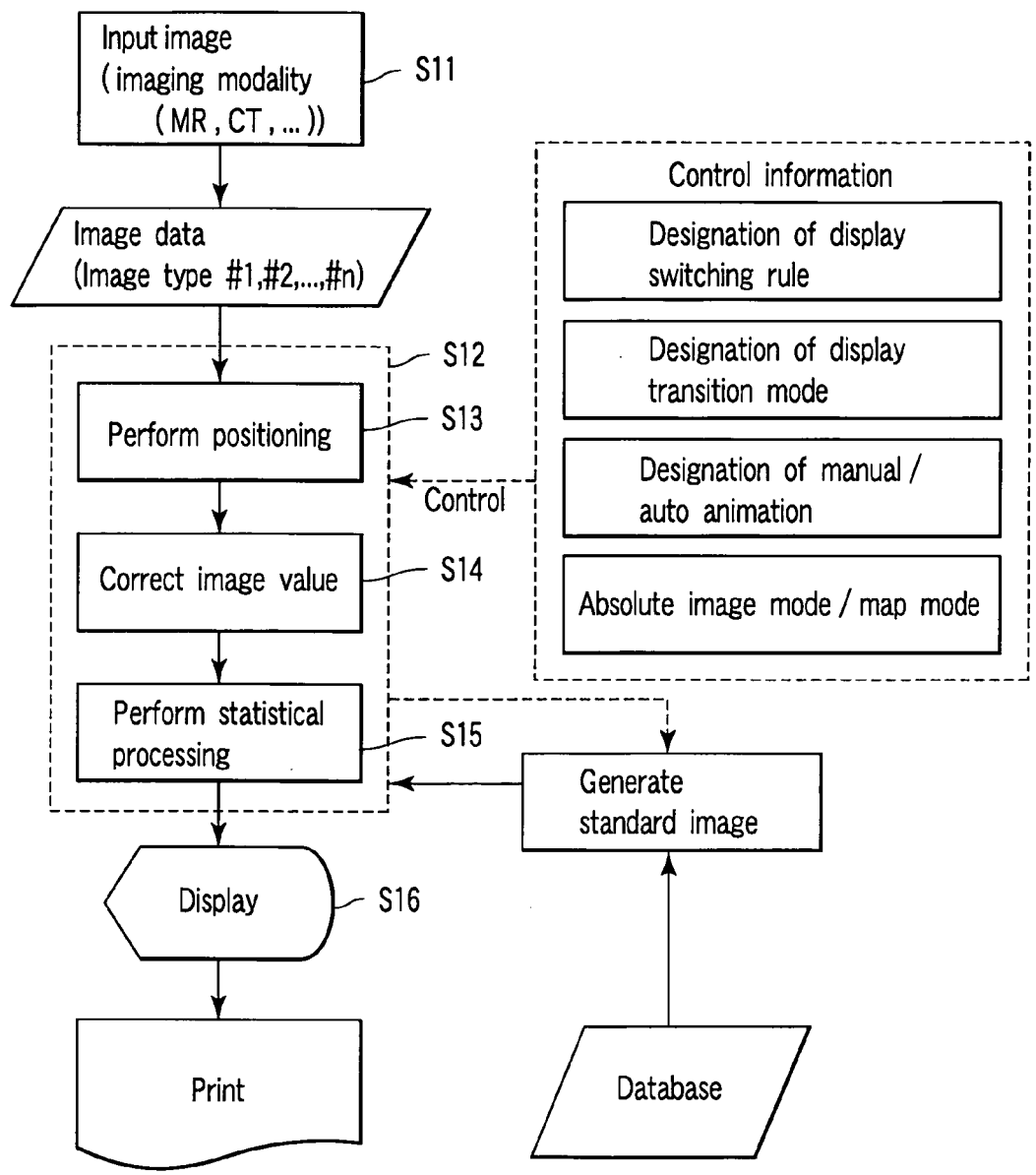
FIG. 4 is a view showing the flow of overall image display processing by the control unit in FIG. 1.

This sequence will be described with reference to the flowchart of FIG. 4. As display target images (interpretation target images), for example, a longitudinal relaxation enhancement image, transverse relaxation enhancement image, and proton density image concerning the same region of the same subject which are acquired by the MRI device with different image parameters are supplied through the communication unit 7, and stored in the image storage unit 2 comprising a magnetic disk or large-capacity semiconductor memory (S11).

Stored display target images are processed by the image processing unit 5 on the basis of control information which is given on-site by the interpreting doctor or is stored in advance. Positioning between the images and pixel value (luminance) correction are performed on the basis of the control information and by referring to standard images in a standard database as needed (S12).

In the case of MRI, since a plurality of types of images can be acquired while a subject to be examined is kept lying on the bed, anatomical positioning can be relatively easily performed as long as a reference is determined, and position correction can be performed relatively easily on the basis of position information attached to image data (S13). Note that although position correction is almost unnecessary if images of the same subject acquired in the same examination process are display targets, re-slicing must be done if different slices are acquired. In addition, even if the same subject is imaged, when current image data is to be matched to past image data, and the shape of each image must be three-dimensionally matched to the reference image in consideration of the slice angle and translation. The suitable reference images are generated. The suitable reference images are selected from standard images stored in the database. The reference images are created on the basis of the display target image and reference numerical value information (reference values of tissues) stored the database. The values of the tissues in the display target image are replaced the reference values of tissues stored the database.

If the same subject is imaged without any deformation, affine transformation for transforming a solid body is sufficient. Even if the same subjects is imaged when deformation with respect to the reference image is large, and if different subjects to be examined are imaged, non-rigid body transformation is required. This technique is executed while control information to be provided by the operator as needed is minimized. If an operation form is determined, the form is set in a file in advance to allow control by only referring to the file.

Normalization processing is performed to suppress variations in pixel value between images due to variations in gain or imaging parameter differences by using a linear function ($y=ax+b$, where x is an input pixel value, and y is an output pixel value) (S14). Methods of determining a and b include a method of calculating them from supplied images and a method using given statistically calculated values. In the case of MRI, if acquisition conditions such as hardware and a reception gain are kept constant, little variation occurs between examination processes. However, some kind of normalization is required for pixel values even when the same device is used under other conditions or images acquired by different types of devices are used.

Display target images having undergone necessary processing such as position correction and deformation are transferred to the display memory of the display control unit 6 and display operation of the display control unit 6 is started (S16). In initial display operation, the display target images are displayed in animation. The images are then displayed under the control of the interpreting doctor or on the basis of preset control information in consideration of the designation of imaging parameters, the display transition mode, the display (switching) speed, the presence/absence of the fade-in/fade-out effect. Such images can be displayed while settings are changed as needed, upon determination by the interpreting doctor. For example, speed control and the like are performed with the mouse, software or hardware dial, or the like. This apparatus also has a function of switching arbitrary images in accordance with operation by the interpreting doctor. It is important to allow the doctor to perform control without looking aside from an image. Hard copies of images can be produced as needed. In the case of spatial multi-slices, parameter types can be switched in synchronism with all the slices. In addition, multi-slice display in the time axis direction can be selected for multi-parameter images acquired in different time axis directions.

Furthermore, the display switching rule based on imaging parameters can be changed to, for example, display switching rules based on a slice direction and time axis direction. Alternatively, these rules can be arbitrarily combined. According to a combination example, as shown in FIG. 3B, after images with different imaging parameters are sequentially switched and displayed, the slice position is moved, and images with different imaging parameters at the position are sequentially switched and displayed. The interpreting doctor can also arbitrarily designate a display direction and a combination of rules. The present invention is not limited to the arrangement of this embodiment. In performing fusion display of known time-series dynamic acquired images and images with different parameters, images can be arbitrarily selected and combined.

Figure 6A:
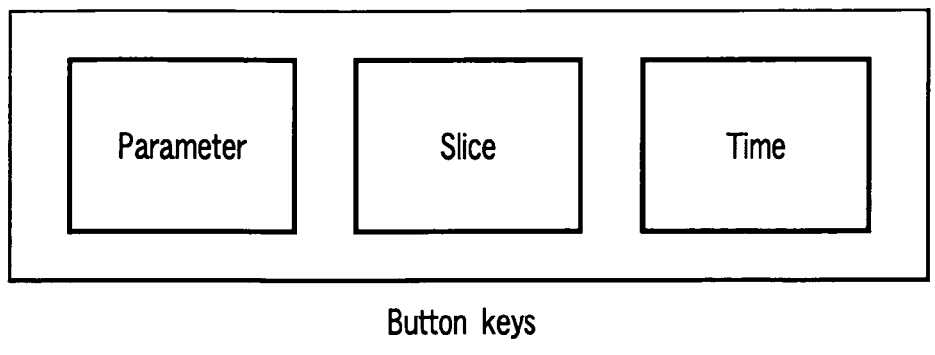
FIGS. 6A and 6B are views showing operation devices for selecting an image switching rule, which are arranged on an input unit in FIG. 1.
Figure 6B:
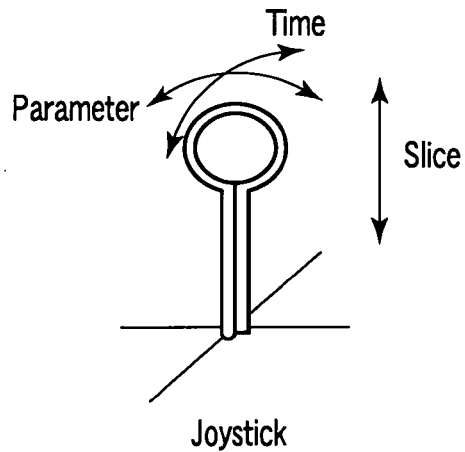
Figure 7:
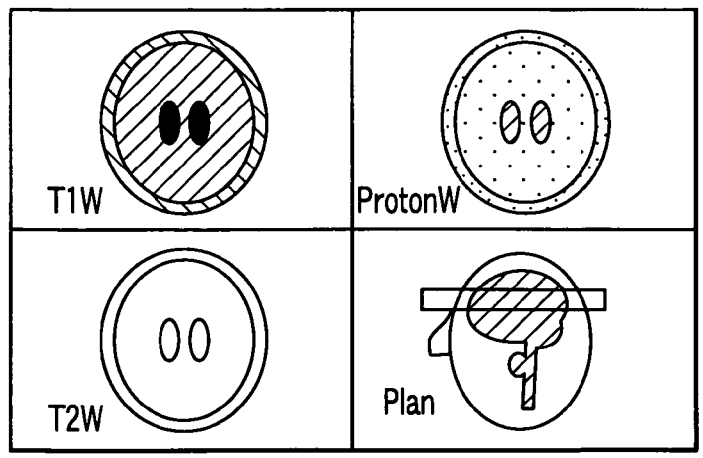
FIG. 7 is a view showing an example of a conventional image display window.

While images with different imaging parameters are switched and displayed, for example, the switching rule based on a time direction or slice direction can be changed to another rule. The interpreting doctor can change three types of switching rules based on imaging parameters, times, and slice positions by using the button keys in FIG. 6A which are arranged on the input unit 4, the joystick in FIG. 6B, or the like without shifting his/her viewpoint from the images. This function allows the interpreting doctor to smoothly perform diagnosing operation.

By properly operating the input unit 4, display of an image or map can be changed to display of a statistical processing result (S15). When a region of interest (ROI) is set in an arbitrary place on an image, statistic values are calculated from pixel values in a display target image or map in the ROI by the ROI processing unit 11, and are numerically displayed or graphically displayed as shown in FIGS. 5A and 5B. Every time a new ROI is set, the display is switched in real time. A hard copy of a graphic display result can be produced as needed.

Note that a point of this embodiment is to have a standard image database reference function. Data levels are set according to subjects to be examined, able-bodied people, and diseases. A normality/abnormality level can be quantitatively diagnosed by comparison with a given standard image. A standard image is not specially required for the absolute value display mode of displaying the original pixel values of an image without any change (information for normalization is required). However, a standard image is required for the generation of a map. According to a reference/comparison method, for example, a map is generated from the ratios between the pixel values of a standard image and those of an interpretation target image.

In this case, when target subject data is close to normal, the corresponding ratio becomes close to 1. Since data has a given statistical variation, the mean value (P value) of pixel values is displayed, together with a graph of the mean value of ratios and a standard deviation SD. When the interpreting doctor assumes given disease data, he/she selects a target disease and checks its statistical distance. The detector selects a target disease exhibiting the nearest Mahalanobis distance by using a plurality of parameters and referring to a database stored in a computer. The Mahalanobis distance is a scale representing a similarity in a multidimensional feature space. Suspicious diseases are presented, together with statistical likelihoods, in order of decreasing possibility. This is a CAD function. For the quantification of comparison results between a database and indexes, Mahalanobis distances between multidimensional vectors based on a theory used for pattern recognition are used. Regarding different types of parameters as vectors, measurement parameter vectors may be used without any change for the analysis of a relationship with a database. If necessary, however, the efficiency of this operation can be improved by using, as a database and comparative data, data having undergone common pre-processing such as dimensional compression using principal component analysis (PCA) or independent component analysis (ICA), which is performed to reduce the number of parameters or enhance the independency among parameter vectors.

It is important for the generation of a map using a standard image to perform anatomical positioning between the standard image and a target image of a subject to be examined.

Positioning is executed in conformity with the form of a standard database or by matching standard data to each subject data. As the spatial resolution increases, individual differences cannot be neglected in matching of details, and hence the significance of the operation decreases. Therefore, comparison is done in large areas. In nuclear medicine, matching to standard data is actually performed by using SPECT or PET. Since the spatial resolution is small enough to produce no individual differences, this technique is successfully executed to some extent.

Database levels are set, with respect to apparatuses, according to a single apparatus, apparatuses of the same model by the same maker, the overall same modality, and different types of modalities with common parameters. In addition, database levels are set, with respect to the sizes of subjects to be examined, according to the same subject, each hospital, municipality, a domestic level, and an internal level in the end. Such a database is accessed through a LAN or the Internet.

The display method of this embodiment is an effective display method associated with MRI for routine acquisition and observation of imaging parameters such as T1 enhancement, T2 enhancement, and proton density parameters, and hence MRI images have been exemplified. However, this method can be applied to display of images based on various types of modalities, other than MRI images, e.g., X-ray CT images, ultrasound images, SPECT images, PET images, and endoscope images, display of images based on a combination of such modalities, and display of industrial images of the same region with different types of parameters such as a temperature distribution, CT value, and an elasticity distribution as well as medical images.

According to this embodiment, at least one of the first to fourth effects can be obtained:
1. Since a plurality of types of images obtained by imaging the same region using various techniques are switched and displayed, like page turning, in the same size at the same position on the screen, the doctor can hardly overlook even a minute change due to a difference in imaging technique while fixing his/her viewpoint at the position of a region of interest on the screen. This makes it possible to improve doctor's diagnostic efficiency and performance and reduce fatigue.
2. Display target images are displayed on the basis of ratios or differences with respect to normal values, and a priority difference assay result obtained by numerical, statistical analysis is also presented as needed. This makes it possible to perform quantitative diagnosis instead of qualitative diagnosis.
3. Since comparison with a reference image generated for each specific disease can be made, the possibility of affection can be grasped numerically. This allows objective diagnosis. Therefore, this technique can be developed into computer aided diagnosis.
4. Since this technique allows numerical comparison with a standard image generated for each specific disease unlike the prior art in which ambiguous qualitative data, i.e., gray-scale information, is used, the possibility of affection can be grasped numerically. This contributes to the development of medical diagnostic treatment based on data. This in turn reduces medical malpractice problems, increases the level of satisfaction of subjects to be examined, and reduces medical expenses. As a consequence, medical treatment based on diagnostic treatment data using images, i.e., evidence-based medicine (IBM), will advance.

In this embodiment, the Medical images concern the same region of the subject, however the Medical images may be images including the same region of the subject. The Medical images may be images including the same region, for different slices.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image display apparatus comprising:
    a memory configured to store data of a plurality of magnetic resonance (MR) slice images that have been generated by a magnetic resonance imaging (MRI) device of a same region of a subject to be examined, said stored MR slice images of the same region all having the same slice orientation but including images which differ from each other by at least one of (a) MRI parameters used to acquire the MR slice images, (b) MR slice image positions within said region of the subject, and/or (c) times at which the MR slice images were acquired;
    control circuitry configured to
        receive said data of the plurality of MR slice images from said memory,
        correct positions of the plurality of MR slice images to anatomically align the plurality of MR slice images by using position information attached to the data of the plurality of MR slice images or by matching to a reference image for the region of the subject so that the positions of anatomical structures in the respective MR slice images match each other, and
        generate and output each of the plurality of MR slice images anatomically aligned, one at a time, to be displayed at a same position on a display screen by sequentially switching generation of the plurality of MR slice images one by one, based on operator selection of a rule for switching based on (a) MRI parameters used to acquire the plurality of MR slice images, (b) MR slice image positions within said region of the subject, or (c) times at which the MR slice images were acquired, so as to make the center of each image coincide with the same position on the display screen; and
    a display having said display screen and connected to sequentially receive each of the plurality of MR slice images anatomically aligned, one at a time, from the control circuitry and alternately display the received MR slice images on the display screen, wherein the center of each of the plurality of MR slice images coincides with the same position on the display screen while also matching the positions of the anatomical structures in the respective alternately displayed MR slice images to each other.

2. An apparatus according to claim 1, wherein the memory stores said plurality of MR slice images as generated by a magnetic resonance imaging (MRI) device using different MR imaging parameters, and
    the control circuitry generates and outputs each of the plurality of MR slice images anatomically aligned, one at a time, based on the MR imaging parameters.

3. An apparatus according to claim 2, wherein the memory stores said plurality of MR slice images as generated by a magnetic resonance imaging (MRI) device using different MRI pulse sequences.

4. An apparatus according to claim 1, wherein the memory stores said plurality of MR slice images as acquired in different time periods, and the control circuitry generates and outputs each of the plurality of MR slice images anatomically aligned, one at a time, along a time period direction.

5. An apparatus according to claim 1, wherein the control circuitry is further configured to generate and output each of the plurality of MR slice images anatomically aligned, one at a time, based on MR imaging parameters by switching said plurality of MR slice images with a fade-in/fade-out effect.

6. An apparatus according to claim 1, wherein the control circuitry is further configured to generate a map having, as pixel values, ratios or differences between pixels of an MR slice image and respectively corresponding pixels of a reference image of the same MR slice region, and to output a map image formed by the pixel values for the map to the display to display the map in place of any of the plurality of MR slice images currently displayed.

7. An apparatus according to claim 6, wherein the reference image is a prior MR slice image of the subject.

8. An apparatus according to claim 6, wherein the reference image is not a prior MR slice image of the subject but, instead, a standard image of the same MR slice region which is statistically processed.

9. An apparatus according to claim 8, wherein a standard image is provided for each of a plurality of diseases.

10. An apparatus according to claim 6, wherein the reference image is derived from an MR slice image of the subject by replacing pixel values therein representing tissue values with determined reference values.

11. An apparatus according to claim 6, wherein the control circuitry is further configured to eliminate or reduce a shift between the MR slice image and the reference image by deformation to generate and output each of the plurality of MR slice images anatomically aligned so that the display alternatively displays the center of each of the plurality of MR slice images that coincides with the same position on the display screen while also matching the positions of the anatomical structures in the respective alternately displayed MR slice images to each other.

12. An apparatus according to claim 1, wherein the control circuitry is configured to generate and output each of the plurality of MR slice images anatomically aligned, one at a time, at predetermined time intervals.

13. An apparatus according to claim 1, wherein the control circuitry is further configured to generate a graphical pattern representing changes (a) between the MR slice images of ratios or differences between pixel values included in regions of interest in the MR slice images and standard values or (b) between the pixel values and the standard values.

14. An apparatus according to claim 1, wherein said plurality of MR slice images include: (a) a longitudinal MR relaxation enhancement image, (b) a transverse MR relaxation enhancement image, and (c) a proton density MR image obtained.

15. An apparatus according to claim 1, wherein said plurality of MR slice images include images obtained at different slice positions and at different imaging times, and the control circuitry is configured to generate and output each of the plurality of MR slice images anatomically aligned, one at a time, along a direction of the slice positions or along a direction of the imaging times selectively based on a user input.

16. An apparatus according to claim 1 wherein the control circuitry is configured to generate and output each of the plurality of MR slice images anatomically aligned, one at a time, by performing a matching process between a reference image and the plurality of MR images in accordance with slice angles and translation.

17. An apparatus according to claim 1 wherein the control circuitry is configured to generate and output each of the plurality of MR slice images anatomically aligned, one at a time, by performing a matching process between a reference image and the plurality of MR images by using at least one of affine transformation for transforming a rigid body and deformation for transforming a non-rigid body.

18. An apparatus according to claim 1 wherein the control circuitry is configured to generate and output each of the plurality of MR slice images anatomically aligned, one at a time, by performing re-slicing of a plurality of MR images when positions of slices thereof are different so as to provide said MR slice images of the same anatomical region all having the same slice orientation.

19. An apparatus according to claim 1 wherein the control circuitry is further configured to perform pixel value correction in each of the plurality of MR slice images by referring to standard images for the region of the subject.

20. An apparatus according to claim 19 wherein the control circuitry is configured to perform pixel value correction in each of the plurality of MR slice images by normalization processing which suppresses variations in pixel value between the plurality of MR slice images due to variations in gain or imaging parameter differences.

21. A medical image display apparatus comprising:
a memory configured to store data of a plurality of magnetic resonance (MR) slice images that have been generated by a magnetic resonance imaging (MRI) device and which include a same region of a subject to be examined, said stored MR slice images of the same region all having the same slice orientation but including images which differ from each other by at least one of (a) MRI parameters used to acquire the MR slice images, (b) MR slice image positions within said region of the subject, and/or (c) times at which the MR slice images were acquired;
control circuitry configured to
receive said data of the plurality of MR slice images from said memory,
correct positions of the plurality of MR slice images to anatomically align the plurality of MR slice images by using position information attached to the data of the plurality of MR slice images or by matching to a reference image for the region of the subject so that the positions of anatomical structures in the respective MR slice images match each other, and
generate and output each of the plurality of MR slice images anatomically aligned, one at a time, to be displayed at a same position on a display screen by sequentially switching data for the plurality of MR slice images anatomically aligned one by one, based on operator selection of a rule for switching based on (a) MRI parameters used to acquire the plurality of MR slice images, (b) MR slice image positions within said region of the subject, or (c) times at which the MR slice images were acquired, so as to make the center of each image coincide with the same position on the display screen; and a display having the display screen and connected to sequentially receive said data for each of the plurality of MR slice images anatomically aligned, one at a time, from the control circuitry and alternately display the MR slice images on the display screen based on the received data, wherein the center of each of the plurality of MR slice images coincides with the same position on the display screen while also matching the positions of the anatomical structures in the respective alternately displayed MR slice images to each other.

22. A medical image display apparatus comprising:
a memory configured to store data including (a) a plurality of magnetic resonance (MR) slice images that have been generated by a magnetic resonance imaging (MRI) device of a same region of a subject to be examined, said MR slice images of the same region all having the same slice orientation, and (b) at least one MR slice image concerning a target other than the subject but representing the same anatomical region as said same region of the subject;
control circuitry configured to
receive the data stored in the memory,
    correct positions of the plurality of MR slice images and the at least one MR slice image concerning the target to anatomically align the plurality of MR slice images and the at least one MR slice image concerning the target by using position information attached to the data of the plurality of MR slice images or by matching to a reference image for the same anatomical region so that the positions of anatomical structures in the respective MR slice images and the at least one MR slice image concerning the target match each other, and
    generate and output each of said plurality of MR slice images anatomically aligned, one at a time, to be displayed at a same position on a display screen by sequentially switching the plurality of MR slice images one by one, based on operator selection of a rule for switching based on (a) MRI parameters used to acquire the plurality of MR slice images, (b) MR slice image positions within said region of the subject, or (c) times at which the MR slice images were acquired, so as to make the center of each image coincide with the same position on the display screen; and
a display having the display screen and connected to sequentially receive each of the plurality of MR slice images anatomically aligned, one at a time, from the control circuitry and alternately display the received MR slice images on the display screen, wherein the center of each of the plurality of MR slice images coincides with the same position on the display screen while also matching the positions of anatomical structures in the respective alternately displayed MR slice images to each other.

23. A medical image display apparatus comprising:
a memory configured to store data including a plurality of magnetic resonance (MR) slice images that have been generated by a magnetic resonance imaging (MRI) device including a same region of a subject to be examined, said stored MR slice images of the same region all having the same slice orientation but including images which differ from each other by at least one of (a) MRI parameters used to acquire the MR slice images, (b) MR slice image positions within said region of the subject, and/or (c) times at which the MR slice images were acquired;
control circuitry configured to
    receive the data of the plurality of MR slice images from the memory,
    correct positions of the plurality of MR slice images to anatomically align the plurality of MR slice images by using position information attached to the data of the plurality of MR slice images or by matching to a reference image for the region of the subject so that the positions of anatomical structures in the respective MR slice images match each other,
    generate and output each of the plurality of MR slice images, one at a time, to be displayed at a same position on a display screen by sequentially switching the plurality of MR slice images one by one, based on operator selection of a rule for switching based on (a) MRI parameters used to acquire the MR slice images, (b) MR slice image positions within said region of the subject, or (c) times at which the MR slice images were acquired, so as to make the center of each image coincide with the same position on the display screen; and
a display having the display screen and connected to sequentially receive each of the plurality of MR slice images anatomically aligned, one at a time, from the control circuitry and alternately display the received MR slice images on the display screen, wherein the center of each of the plurality of MR slice images coincides with the same position on the display screen while also matching the positions of anatomical structures in the respective alternately displayed MR slice images to each other.

24. A medical image display apparatus comprising:
a memory configured to store data including a plurality of magnetic resonance (MR) slice images that have been generated by a magnetic resonance imaging (MRI) device concerning a same region of a subject to be examined, said stored MR slice images of the same region all having the same slice orientation but including images which differ from each other by at least one of (a) MRI parameters used to acquire the MR slice images, (b) MR slice image positions within said region of the subject, and/or (c) times at which the MR slice images were acquired;
control circuitry configured to
    receive the data of the plurality of MR slice images from the memory,
    correct positions of the plurality of MR slice images to anatomically align the plurality of MR slice images by using position information attached to the data of the plurality of MR slice images or by matching to a reference image for the region of the subject so that the positions of anatomical structures in the respective MR slice images match each other,
    generate and output each of said plurality of MR slice images anatomically aligned to be displayed at a same position on a display screen by sequentially switching the plurality of MR slice images one by one, based on operator selection of a rule for switching based on (a) MRI parameters used to acquire the MR slice images, (b) MR slice image positions within said region of the subject, or (c) times at which the MR slice images were acquired, so as to make the center of each image coincide with the same position on the display screen; and
a display having the display screen and connected to sequentially receive each of the plurality of MR slice images anatomically aligned, one at a time, from the control circuitry and alternately display the received MR slice images on the display screen, wherein the center of each of the plurality of MR slice images coincides with the same position on the display screen while also matching the positions of the anatomical structures in the respective alternately displayed MR slice images to each other.

* * * * *